United States Patent [19]

Gocho

[11] 4,456,037
[45] Jun. 26, 1984

[54] PROCESS OF DELIVERING SAMPLES AND REAGENTS

[75] Inventor: Nagahiro Gocho, Hachioji, Japan

[73] Assignee: Olympus Optical Company Limited, Japan

[21] Appl. No.: 352,156

[22] Filed: Feb. 25, 1982

Related U.S. Application Data

[63] Continuation of Ser. No. 139,757, Apr. 14, 1980, abandoned.

[30] Foreign Application Priority Data

Apr. 19, 1979 [JP] Japan .................................. 54-48199

[51] Int. Cl.$^3$ .......................... B65B 3/04; B67C 3/02
[52] U.S. Cl. .......................................... 141/1; 141/9; 141/91; 141/130; 134/21; 422/64; 422/100
[58] Field of Search ........................ 141/1-12, 141/85-92, 129, 130, 250-285; 134/21, 22.1, 22.11, 22.12, 131; 422/63, 65, 100, 64

[56] References Cited

U.S. PATENT DOCUMENTS 3,193,358  7/1965  Baruch .................................. 422/64
3,687,632  8/1972  Natelson ............................. 422/100

Primary Examiner—Houston S. Bell, Jr.
Attorney, Agent, or Firm—Parkhurst & Oliff

[57] ABSTRACT

A process of delivering a given amount of a sample and one or more reagents into a reaction vessel by means of a common delivery device which includes a single aspiration-discharge pump and a single probe, without contamination between samples and reagents, wherein a washing step of clearing an outer surface of the probe chip by immersing it into a wash-water, preferably a diluent, is introduced between an aspiration step and a discharge step or between the discharge step and the aspiration step.

8 Claims, 4 Drawing Figures

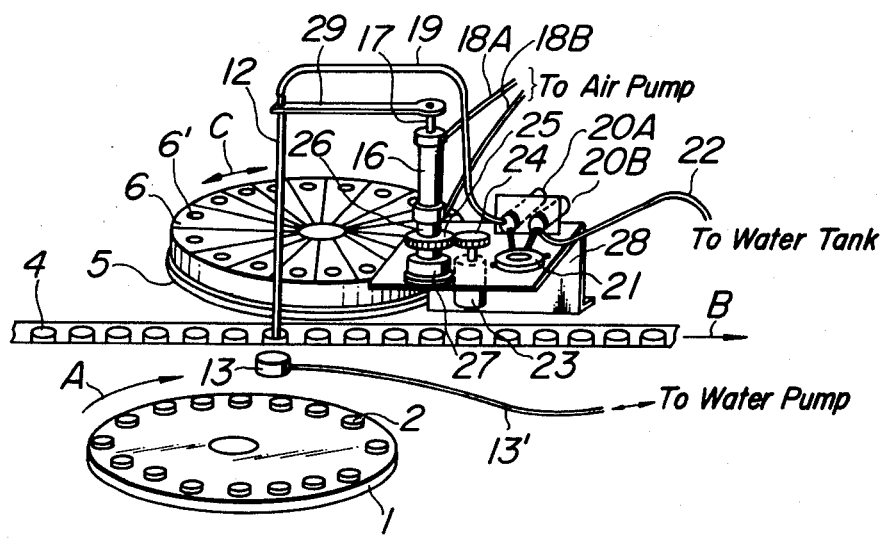
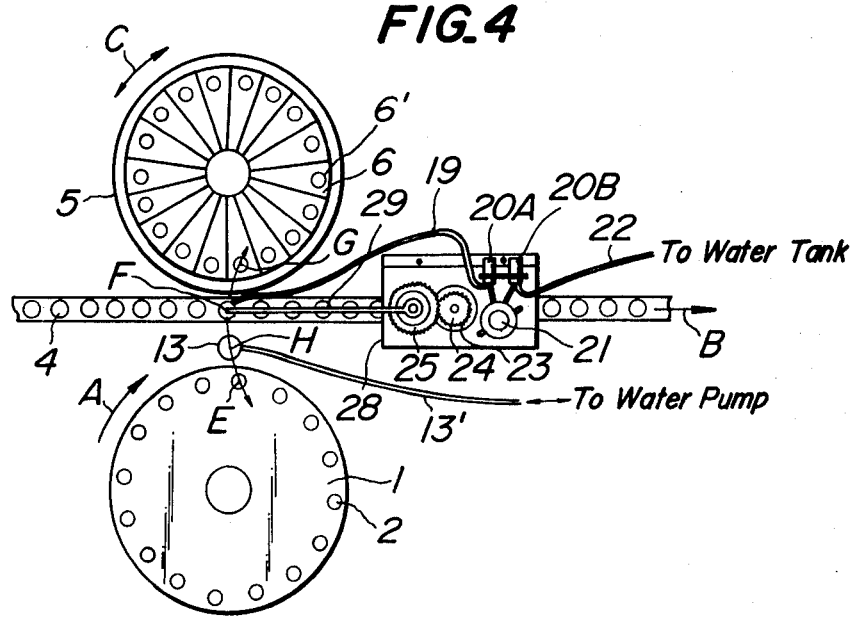

180
PROCESS OF DELIVERING SAMPLES AND REAGENTS

This is a continuation of application Ser. No. 139,757 filed Apr. 14, 1980, which is now abandoned.

BACKGROUND OF THE INVENTION

This invention relates to a process of delivering samples and reagents into reaction vessels by means of a common delivery device.

In known automatic chemical analyzers there are separately provided a sample delivery device for delivering a given amount of sample liquid into a reaction vessel, and a reagent delivery device for delivering a given amount of reagent into the reaction vessel. In analyzers in which a plurality of test items can be measured, since a number of different kinds of reagents corresponding to the number of test items must be used, a plurality of reagent delivery devices are generally provided in order to avoid possible contamination between the reagents. Therefore, the analyzers are liable to be complicated in construction and operation and to be expensive in cost.

SUMMARY OF THE INVENTION

The present invention has for its object to provide a novel and useful process of delivering samples and reagents by means of a single delivery device without contamination between the samples and reagents.

According to the invention a process of delivering samples and reagents into reaction vessels by means of a common delivery device comprises a step for aspirating a given amount of a sample into the delivery device;

a step of discharging the aspirated sample into a reaction vessel;

a step of aspirating a given amount of a given desired reagent into the delivery device;

a step of discharging the aspirated reagent into the reaction vessel; and a step of washing a probe or a liquid path connected to the probe of the delivery device with wash water or diluent, this washing step being interposed between the sample or reagent aspirating step and the sample or reagent discharging step.

BRIEF DESCRIPTION OF THE DRAWINGS

FIG. 3 is a perspective view depicting another embodiment of the delivery device for use in the delivery process according to the invention; and FIG. 4 is a plan view showing the delivery device of FIG. 3.

DESCRIPTION OF THE PREFERRED EMBODIMENTS

Figure 1:
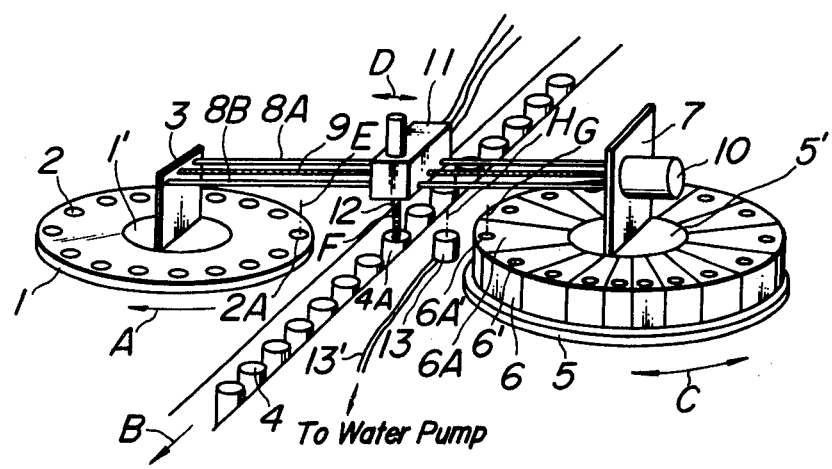
FIG. 1 is a perspective view showing an embodiment of a delivery apparatus for carrying out the delivery process according to the invention.

FIG. 1 is a perspective view showing an embodiment of a delivery device for carrying out the delivering process according to the invention. A sample turntable 1 holds a number of sample cups 2 along its periphery and is rotated about a bearing 1' in a direction shown by an arrow A. The sample turntable 1 is rotated intermittently at a given pitch in accordance with patient test item information which has been input in an analyzer. On the bearing 1' is secured a post 3. A number of reaction vessels 4 are advanced along a reaction lane intermittently in a direction shown by arrow B in synchronism with analyzing steps. A reagent turntable 5 is arranged on an opposite side to the sample turntable 1 with respect to the reaction lane, and a plurality of, in the instant embodiment six, reagent containers 6 are placed on the reagent turntable 5. Each reagent container 6 has formed therein an opening 6' through which a probe of a delivery device can pass. The openings 6' are so formed that they are aligned along a circle. The reagent turntable 5 is rotated in both directions as shown by a double-headed arrow C by means of a suitable driving mechanism (not shown). Any desired reagent container 6 can be indexed at a delivery position. On a bearing 5' for journaling the reagent turntable 5 is secured a post 7. Between the posts 3 and 7 are fixedly arranged guide rails 8A and 8B. Further a feed screw 9 is rotatably arranged between the posts 3 and 7. A reversible motor 10 is fixedly arranged on the post 7 and its driving shaft is connected to one end of the feed screw 9. Through the guide rails 8A, 8B and the feed screw 9 is arranged a slide box 11. When the motor 10 is energized to drive the feed screw 9, the slide box 11 is slidden in both directions as illustrated by a double-headed arrow D. In the slide box 11 is arranged a delivery device and its probe 12 is moved up and down. The slide box 11 is indexed and stopped at a sample aspiration position E, a discharge position F, a reagent aspiration position G and a probe washing position H. In this embodiment the probe washing position H is set between the reagent aspiration position G and the discharge position F. At this position H is arranged a washwater container 13, and wash water can be flowed into and exhausted from the container 13.

Figure 2:
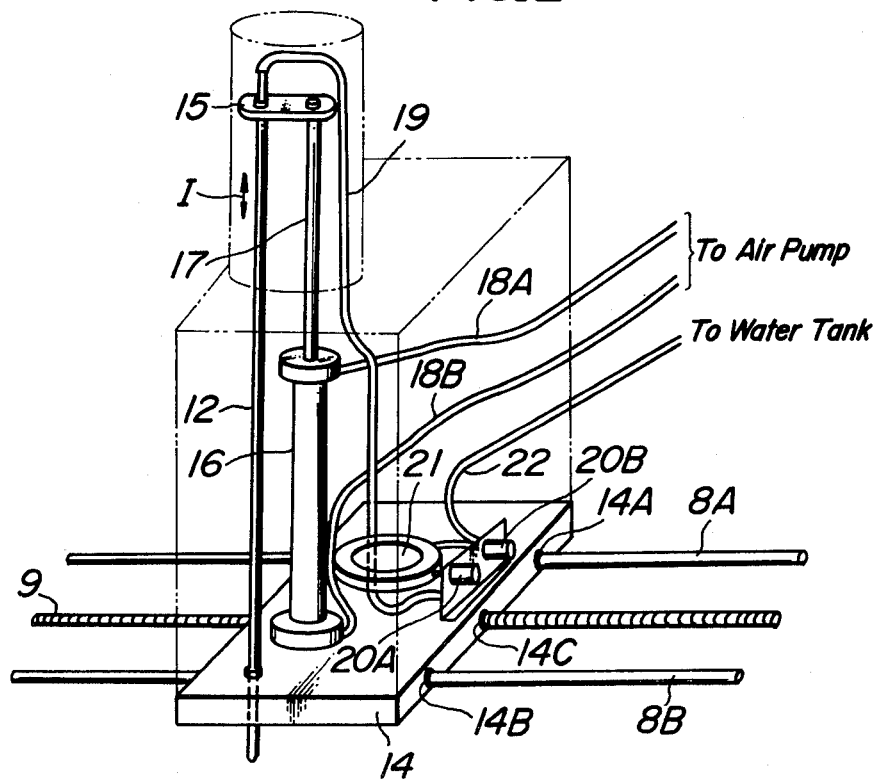
FIG. 2 is a perspective view illustrating an inner construction of a slide box shown in FIG. 1.

FIG. 2 is a perspective view illustrating an internal construction of the slide box 11. The guide rails 8A and 8B are freely inserted into through holes 14A and 14B, respectively formed in a base plate 14 of the slide box 11. The feed screw 9 is engaged with a female screw 14C formed in the base plate 14. In order to move the probe 12 up and down as shown by the double-headed arrow I, a rear end of the probe 12 is coupled with a connector 15 which is connected to a piston 17 of an air cylinder 16. The air cylinder 16 is communicated through tubes 18A and 18B and a change-over valve (not shown) with an air compressor (not shown). By actuating the change-over valve at suitable timings, the piston 17 can be moved up and down. The probe 12 is communicated through a flexible tube 19 and an input-side solenoid valve 20A to a miniature piezo-pump 21. The pump 21 is further communicated through an output-side solenoid valve 20B and a tube 22 with a washwater tank (not shown).

Now, the operation of the delivery device will be explained. At first, the piezo-pump 21 and solenoid valves 20A and 20B will be described. While the input-side solenoid valve 20A and is opened and the output-side solenoid valve 20B is closed, when the piezo-pump 21 is driven by applying to it a positive voltage, a given constant amount of liquids can be introduced into the pump 21. Then the piezo-pump 21 is energized with a negative voltage, while the input-side solenoid valve 20A is closed and the output-side solenoid valve 20B is opened, the liquid aspirated in the pump 21 is discharged to the output-side. In this manner a given amount of the liquid can be flowed from the input-side to the output-side. When the order of opening and closing the solenoid valves 20A and 20B are reversed, the fluid may be flowed in a reverse direction. That is to say, by using the above mentioned delivery mechanism it is possible to deliver the fluid in two different modes, i.e. in a first mode the liquid is aspirated from the input-side and is discharged to the output-side, and in a second mode the liquid is aspirated from the output-side and is discharged to the input-side. In the first mode of operation the liquid flows through the whole liquid path of the pump system and thus, when delivering a plurality of different kinds of liquids, the whole liquid path has to be washed. Further the liquid path should be filled with the given amount of liquid and an additional amount of liquid, and the additional amount of liquid is wasted. On the contrary, in the second mode a given desired amount of liquid is aspirated into the pump system, and then the aspirated liquid can be discharged. Therefore, the additional liquid would not be wasted and the liquid path is made in contact with the liquid to the minimum extent. Under the above circumstance, in the present embodiment the second mode of the operation is adopted. The output-side of pump system is coupled with water or diluent. Prior to the delivery the whole liquid path is filled with water by repeating the following operation; while the output-side valve 20B is opened and the input-side valve 20A is closed, the piezo-pump 21 is operated to aspirate therein a given amount of water, and then after the output-side valve 20B is closed and the input-side valve 20A is opened, the pump 21 is operated again. In this manner water can be introduced into the pump system up to a chip of the probe 12. If there is an air layer in the liquid, the delivery amount of liquid might be inaccurate due to expansion and compression of air. Further the whole liquid path including the probe 12 can be washed by discharging water from the probe 12.

Now the operation of whole apparatus will be explained. In an initial condition the slide box 11 is situated at the washing position H above the wash-water container 13 and the probe 12 is in its upper position. The sample turntable 1 is rotated, and a sample cup which contains a sample liquid to be delivered is indexed at the sample delivery position E. During this step the motor 10 is driven in the given direction to move the slide box 11 into the sample aspiration position E above the sample container. The motor 10 may be controlled in the following manner. When the motor 10 is a pulse motor, the number of pulses corresponding to the indexed positions of the slide box 11 have been previously stored in a control circuitry. At a given desired position, for instance, the initial position H, is determined as a reference position and a position detector such as a micro-switch is arranged at the reference position so as to detect that the slide box 11 is in the reference position. Then, the position control of the slide box 11 can be performed by calculating the number of pulses supplied to the pulse motor.

When use is made of a D.C. or A.C. motor as the motor 10, the position of the slide box 11 can be detected by counting output pulses from a rotary encoder coupled to the feed screw 9, or by arranging opto-electronic position detecting switch or microswitches at the indexed positions of the slide box 11.

Then the piston 17 is moved downward by the air cylinder 16 and the chip of the probe 12 is immersed in the sample liquid contained in the sample cup 2A currently situated at the position E. Then the piezo-pump 21 and solenoid valves 20A and 20B are so driven to aspirate a given amount of the sample into the probe 12.

Then the air cylinder 16 is operated to move the piston into its upper position and thus, the probe 12 is also raised out of the sample cup 2A.

Next the motor 10 is energized to move the slide box 11 into the washing position H and is stopped above the wash-water container 13. Now, the air cylinder 16 is once again operated to move the piston 17 downwards, and the delivery probe 12 is immersed in wash-water contained in the bottle 13 to wash the outer wall of the chip of probe 12. Then the piezo-pump 21 and the solenoid valves 20A and 20B are so driven to aspirate a small amount of water in the chip of probe 12. Owing to the washing and aspiration of water it is possible to avoid contamination of reagents due to the sample liquid adhering to the outer wall of the probe chip. It is preferable to supply fresh water to the wash-water container 13 through the tube 13' every time the washing operation is performed.

After washing the air cylinder 16 is operated to move the piston 17 upwards and the delivery probe 12 is raised out of the washing bottle 13. Then the slide box 11 is moved into the reagent aspiration position G by driving the motor 10. During this movement the reagent turntable 5 is rotated to index a given desired reagent bottle 6A containing a desired reagent to be mixed with the relevant sample into the reagent aspiration position G. In this condition the opening 6A' of the bottle 6A is situated just below the probe 12. Then the piston 17 is moved downwards by the air cylinder 16, and the chip of the probe 12 is immersed in the reagent contained in the reagent bottle 6A. Now the pump 21 and the solenoid valves 20A and 20B are operated to aspirate a given desired amount of the reagent.

Next, the probe 12 is moved upwards out of the reagent bottle 6A by means of the air cylinder 16 and the piston 17. Then the slide box 11 is moved into the discharge position F above the reaction vessel 4A which is currently situated in this position F. The piezo-pump 21 and the solenoid valves 20A and 20B are so driven that the previously aspirated reagent, water and sample are successively discharged in the reaction vessel 4A in this order. It should be noted that it is also possible to discharge a given amount of water or diluent in the reaction vessel 4A through the probe 12. Then the inner wall of the probe 12 can be washed.

Next, the slide box 11 is moved into the washing position H above the wash-water container 13, and then the chip of the probe 12 is immersed in the wash-water in the container 13 to wash the outer wall of the probe 12. While the probe chip is immersed in the wash-water, the piezo-pump 21 and the solenoid valves 20A and 20B may be so operated that the wash-water is successively aspirated and discharged through the probe 12 to wash the inner wall of the probe 12. In this case the washing operation during the discharging step may be dispensed with. Then the delivery probe 12 is moved upwards by driving the air cylinder 16 out of the wash-water container 13 into the initial position.

In the manner explained above one delivery cycle is completed. The position, movement, situation, etc. of various elements during the delivery operation can be summarized in the following table.

| Position of slide box 11 | Position of probe 12 | Piezo-Motor 21 | Valve 20A | Valve 20B |
|---|---|---|---|---|
| Washing position H | Upper ↓ ↓ ↓ ↓ | Operated to aspirate ↓ Operated to discharge ↓ (repeat several times) | Closed ↓ Open ↓ ↓ | Open ↓ Closed ↓ ↓ |
| Sample aspiration position E | Lower | Operated to aspirate | Open | Closed |
| Washing position H | Upper Lower | None | Closed | Closed |
|  |  | Operated to aspirate | Open | Closed |
| Reagent aspiration position G | Upper Lower | Operated to aspirate | Open | Closed |
| Discharge position F | Upper | Operated to discharge | Closed Open | Closed |
| Washing position H | Lower | Operated to aspirate and discharge | Closed Open | Closed |

During each delivery cycle a succession of reaction vessels 4 is advanced by one step except for the discharge step. If the relevant sample has to be further delivered for performing another one or more test items, the sample turntable 1 is not rotated and the above delivery cycle is repeated by given desired times. When the delivery for effecting the desired test items for the relevant sample has been completed, the sample turntable 1 is advanced by one step and a sample vessel containing a sample to be delivered next is indexed into the sample aspiration position E.

The delivery process according to the invention is not limited to the embodiment explained above, but many modifications can be conceived. For instance, in the above embodiment the sample is first aspirated, but the reagent may be first aspirated and then the sample may be aspirated. In the above embodiment only one kind of reagent is aspirated, but more than two kinds of reagents may be aspirated. In this case the washing step may be introduced between the successive reagent aspiration steps. Further during this intermediate washing step a small amount of water or diluent may be aspirated into the probe. In this manner the reagents can be protected against mutual contamination. Further the wash-water container 13 may be arranged on the reagent turntable 6. Then the washing position H will coincide with the reagent aspiration position G and thus, the positional control of the slide box 11 may be much simpler. In the above embodiment the sample and reagent are discharged in the same discharging step, but the aspiration and discharge of the sample and those of the reagents may be effected independently. For instance, the following delivery process may be performed; sample aspiration→sample disharge→washing-→reagent aspiration→reagent discharge→washing.

FIGS. 3 and 4 show another embodiment of the delivery device for carrying out the delivery process according to the invention. In this embodiment portions similar to those of the previous embodiment are denoted by the same reference numerals as those in FIGS. 1 and 2. Constructions and operations of a sample turntable 1 including a number of sample cups 2, a reaction lane along which a succession of reaction vessels 4 can be advanced, a reagent turntable 5 supporting a plurality of reagent bottles 6, solenoid valves 20A and 20B and a piezo-pump 21 communicated with a probe 12, and an air cylinder 16 and its piston 17 for moving the probe up and down, are entirely the same as those of the embodiment of FIGS. 1 and 2. In this embodiment a wash-water bottle 13 is arranged between the sample turntable 1 and the reaction lane. In order to rotate the probe 12 between a sample aspiration position E and a reagent aspiration position G, a motor 23 is secured to a base plate 28 and a gear 24 is fixed to a driving shaft of the motor 23. A gear 25 is engaged with the gear 24 and is secured to a shaft 26 to which the air cylinder 16 is fixed. The shaft 26 is journaled to the base plate 28 by means of a bearing 27. When the motor 23 is driven, the air cylinder 16 and thus an arm 29 connected to the piston 17 are rotated. The probe 12 is secured to a free end of the arm 29. In this manner the probe 12 can be rotated along an arcuate path as shown in FIG. 4, along said path the sample aspiration position E, washing position H, discharge position F and reagent aspiration position G being arranged.

Since the operation of the delivery device of the present embodiment is substantially the same as that of the previous embodiment, only the operation related to the probe washing will be explained. After a given amount of a sample has been aspirated in the probe 12 at the position E, the motor 23 is so energized to rotate the arm 29 and the probe 12 is moved into the washing position H. Then, the air cylinder 16 is driven, and the probe 12 is immersed into the wash-water contained in the bottle 13, so that the sample adhering onto the outer wall of the probe 12 is washed away. During this step the piezo-pump 21 and the solenoid valves 20A and 20B are so operated that a small amount of the wash-water is aspirated into the chip of the probe. Thanks to the washing and aspiration of wash-water, the contamination due to the liquids adhering to the probe 12 can be effectively avoided. It is preferable to supply a fresh wash-water to the bottle 13 every time the washing step is performed. If the probe 12 could not be completely cleaned only by immersing the probe into the wash-water, the following steps may be added; (1) a flow of wash-water is produced in the bottle 13 by means of a tube 13', (2) the probe 12 is vibrated in the bottle 13 by repeatedly driving the motor 23 in forward and backward directions to a small extent, and (3) the probe 12 is moved up and down in the bottle 13 by driving the air cylinder 16. During such a washing step if a part of the liquid which has been already aspirated into the probe 12, might flow into the wash-water, a very small amount of wash-water can be advantageously aspirated in the probe chip prior to the washing.

As explained above in the delivery process according to the invention any desired liquids can be accurately delivered by means of a single delivery device without mutual contamination due to carry-over of liquids. As compared with known delivery systems using a plurality of delivery devices for independently delivering the samples and reagents, the delivery device for use in the present invention has only one probe and one aspiration pump, and has a very simple construction. Further by introducing the washing step between the aspiration step and the discharge step, contamination due to carry-over can be effectively avoided. In this manner the delivery process according to the invention can greatly contribute to simplification of delivery process, miniaturization of delivery apparatus, high reliability, high cost performance, etc.

What is claimed is:

1. A process of delivering each of successive samples and at least one reagent selected from a plurality of reagents into each of successive reaction vessels by means of a common delivery device comprising:
   a step of aspirating a given amount of a sample into a probe of the delivery device;
   a step of discharging the aspirated sample into a reaction vessel;
   a step of aspirating a given amount of a given desired reagent selected from the plurality of reagents into the probe of the delivery device;
   a step of discharging the aspirated reagent into the reaction vessel; and
   a step of washing inner and outer walls of the probe or a liquid path connected to the probe of the delivery device with wash-liquid or diluent, the washing of the outer wall of said probe being effected by moving the probe in the wash-liquid or diluent, and this washing step being interposed between the sample or reagent aspirating step and the sample of reagent discharging step.

2. The process according to claim 1, wherein the aspirated sample and reagent are simultaneously discharged and the washing step comprises first and second washing steps, the first washing step for washing mainly the outer wall of the probe being performed between the sample and reagent aspirations and the second washing step being effected after the discharge of the sample and reagent.

3. The process according to claim 1, wherein at least two different kinds of reagents are aspirated and the washing step is performed between these reagent aspiration steps.

4. The process according to claim 1, wherein the washing step is performed after the sample discharge, but before the reagent aspiration.

5. The process according to claim 1, wherein the washing step is performed after the reagent discharge, but before the sample aspiration.

6. The process according to claim 1, wherein the washing step is performed by immersing the probe in a wash-liquid contained in a bottle.

7. The process according to claim 6, wherein a flow of wash-liquid or diluent is formed in the bottle, while the probe is immersed in the wash-liquid or diluent.

8. The process according to claim 6, wherein during the washing step a small amount of the wash-liquid or diluent is aspirated in the probe, while the probe is immersed in the wash-liquid or diluent.

* * * * *